United States Patent [19]

Pruess et al.

[11] 3,939,139
[45] Feb. 17, 1976

[54] NEW ANTIBIOTIC X-1092

[75] Inventors: David Pruess; James Parnell Scannell, both of North Caldwell, N.J.

[73] Assignee: Hoffmann-La Roche Inc., Nutley, N.J.

[22] Filed: Sept. 9, 1974

[21] Appl. No.: 504,598

[52] U.S. Cl. .................. 260/112.5 R; 195/80 R
[51] Int. Cl.² .................. C07C 103/52; C12B 1/00
[58] Field of Search .......... 260/112.5, 514 H, 557 R

[56] References Cited
OTHER PUBLICATIONS

Erickson et al.: Chem. Abstr. 74:124547f (1971).
Anderson et al.: Chem. Abstr. 73:127102x (1970).

*Primary Examiner*—Lewis Gotts
*Assistant Examiner*—Reginald J. Suyat
*Attorney, Agent, or Firm*—Samuel L. Welt; Bernard S. Leon; Frank P. Hoffman

[57] ABSTRACT

The invention relates to a new and useful antibacterial substance which is of the formula

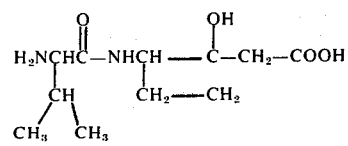

and to processes for its production and recovery. The invention embraces this antibacterial agent and its salts as crude concentrates, as purifed solids and in pure crystaline forms. This antibiotic of the Formula I is effective in inhibiting the growth of gram positive bacteria. The compound of the Formula I is prepared by cultivating a strain of *Streptomyces* sp. X-1092 in an aqueous carbohydrate solution containing a nitrogenous nutrient under submerged aerobic conditions until substantial activity versus Gram-positive bacteria is imparted to said solution and then recovering said compound of the Formula I from said solution.

1 Claim, No Drawings

NEW ANTIBIOTIC X-1092

DETAILED DESCRIPTION OF THE INVENTION

There is provided, according to the present invention, an antibiotic substance effective in inhibiting the growth of Gram-positive bacteria which is of the Formula I. Chemically, this substance is known at 1-(S)-hydroxy-2-(S,S)-valylamido-cyclobutane-1-acetic acid.

There is further provided according to the present invention, a process for the production of such antibiotic substance of the Formula I which comprises cultivation of a strain of *Streptomyces* sp. X-1092 in an aqueous carbohydrate solution containing a nitrogenous nutrient under submerged aerobic conditions until substantial activity versus gram-positive bacteria is imparted to said solution and then recovering said compound of the Formula I from said solution.

The organism producing the antibiotic of the present invention is a new species designated *Streptomyces* sp. X-1092. A culture of the living organism, given the laboratory designation X-1092, has been deposited in the U.S. Department of Agriculture, Agriculture Research Service, NRRL, Peoria, Illinois, and added to its permanent collection of microorganisms as NRRL 8047.

The representative strain of *Streptomyces* sp. X-1092 has the following characteristics.

On solid media, this organism grows in a fashion that is characteristic for members of the genus *Streptomyces*: abundant mycelial growth penetrates into the agar, and the aerial mycelium breaks up in characteristic chains of spores while there is no fragmentation of the immersed mycelium. The aerial sporulation system belongs to the type retinaculum-apertum (RA), with loose spirals, loops and hooks of small diameter.

The formulation of the media used in the description of the growth characteristics, is described below.

Medium 1: "Fermentation medium": Difco Bacto Thermoactinomyces fermentation medium to which 1.5% agar was added.

Medium 2: BBL (Baltimore Biological Laboratory) Czapek-Dox, to which 1.5% agar was added.

Medium 3: Difco Bacto potato dextrose agar.

Medium 4: "Y+M medium": yeast extract, 0.4%; malt extract, 1.0%; dextrose, 0.4%; agar, 2%; pH 7.3.

Medium 5: "Oatmeal-glucose medium": Gerber's oatmeal, 5%; dextrose, 2%; agar 2% in tap water; pH 7.0.

Medium 6: "Tomato paste medium": dextrose, 1% $K_2HPO_4$, 0.1%; tomato paste, 2%; Wilson's Medopeptone, 0.1%; $CaCO_3$, 0.2%; agar, 1.5% in tap water; pH 6.8–7.3.

Medium 7: "Tomato-soy medium": same as medium 6, to which 1% soyalose (Central Soya Co.) has been added.

Medium 8: "Pablum medium": 6% Pablum mixed cereal in cheesecloth bag dipped in and out of boiling tap water for 2 or 3 minutes. The water lost by evaporation is replaced, and agar is added to 1.5%.

Medium 9: "Tomato-oatmeal medium": baby oatmeal (Gerber's), 2%; tomato paste, 2%; agar, 2%, in tap water; pH 6.8–7.3.

Medium 10: "Yeast extract medium": yeast extract, 1%; dextrose, 1%; agar, 1.5%, in tap water; pH 6.8.

Medium 11: "Glucose-asparagine medium": dextrose, 1%; asparagine, 0.05%; $K_2HPO_4$, 0.05%; agar, 1.5%; pH 6.8.

Medium 12: "Glycerol-asparagine medium": glycerol, 1%; asparagine, 0.1% $K_2HPO_4$, 0.1%; agar, 2% in tap water; pH 7.0.

Medium 13: "Starch-casein medium": soluble starch, 1%; casein, 0.1%; $K_2HPO_4$, 0.05%; $MgSO_4$, 0.05%; agar, 1.5%; pH 7.4.

Medium 14: "Emerson's medium": beef extract, 0.4%; peptone, 0.4%; NaCl, 0.25%; yeast extract, 0.1%; dextrose, 1%; agar, 2%; pH 7.0.

Medium 15: "Bennett's medium": yeast extract, 0.1%; beef extract, 0.1%; N-Z-Amine A (casein hydrolysate from Sheffield Inc.) 0.2%; dextrose, 1%; agar, 1.8%; pH 7.3.

Medium 16: "Amidex medium": Amidex (Corn Products Co., Decatur, ILL. 1%; N-Z-Amine A, 0.2%; beef extract, 0.1%; yeast extract, 0.1%; $CaCl_2,2H_2O$, 0.0014%; agar, 2%; pH 7.3.

Medium 17: "Sporulation medium" (ATCC medium number 5): yeast extract, 0.1%; beef extract, 0.1%; tryptose 0.2%; glucose, 1%; $FeSO_4$, trace; agar, 1.5%; pH 7.2.

Media 18, 19, 20, 21, 22, 23 are, respectively, media 2 through 7 as described by Shirling, E. G., and Gottlieb, D., Methods for characterization of *Streptomyces* species, International J. of Systematic Bacteriol., 16, 313–340, 1966.

Unless otherwise indicated, the observations reported have been performed after a period of incubation of 14 days at 28° C. The characteristics of growth in these solid media is summarized in the Table below. Colors of upper surface and reverse are named according to Ridgway's Color Standards and Color Nomenclature, Washington, D.C., 1912.

| Medium | Characteristics of aerial growth | Color of upper surface of colonies | Color of reverse of colonies |
|---|---|---|---|
| 1 | abundant; wrinkled; good sporulation | pallid quaker drab turning to medium deep mouse gray toward the edges; whitish edges | dirty cream buff center turning to dark olive and pale olive buff toward the edges |
| 2 | fair; flat, thin sporulation | whitish | whitish |
| 3 | almost none | | |
| 4 | abundant; wrinkled; good sporulation; medium becomes yellow; droplets of yellow exudate on colonies | pale mouse gray | dirty olive ocher |
| 5 | none | | |
| 6 | abundant; wrinkled; granulated; sporulation thicker | light mouse gray, with whitish edges | honey yellow center and light brownish olive toward the |

-continued

| Medium | Characteristics of aerial growth | Color of upper surface of colonies | Color of reverse of colonies |
|---|---|---|---|
| | at the edges; yellow pigment diffuses into medium | | edges, with mustard yellow edges |
| 7 | abundant; wrinkled; with good sporulation; medium turns light yellow | pale mouse gray; off-white edges | pale mouse gray center, mouse gray toward the edges, and off-white edges |
| 8 | abundant; wrinkled; granulated, good sporulation | pale mouse gray and off-white edges | mustard yellow center turning buffy citrine at edges |
| 9 | abundant; wrinkled; granulated; good sporulation; traces of light yellow pigmentation in the medium | light mouse gray with off-white edges; later mouse gray with gray edges | honey yellow center turning light brownish olive toward the edges |
| 10 | abundant; wrinkled; good sporulation; antimony-yellow exudate; yellow diffusible pigment | light mouse gray with off-white edges which in time became pallid mouse gray | antimony yellow, and in parts, ochraceous tawny |
| 11 | good; wrinkled; scanty sporulation off-white in color | barium yellow vegetative mycelium | citron yellow |
| 12 | abundant; thin sporulation, white in color; colonies granular, cracking with age; light yellow diffusible pigment | cream color vegatative mycelium; later, pallid mouse gray to light mouse gray, with off-white edges | primuline yellow |
| 13 | abundant; light sporulation; yellow pigment produced; clearing around the colonies (hydrolysis of starch and/or casein) | vegetative mycelium primrose yellow; sporulated areas pallid mouse gray with off-white edges | barium yellow |
| 14 | abundant; fairly abundant sporulation | vegetative mycelium Naples yellow; spore areas pallid mouse gray turning off-white at the edges | dirty mustard yellow center turning dirty buffy brown and Naples yellow at the edges |
| 15 | abundant; and good sporulation, which is thinner at the center of colonies; drops of exudate on colonies; light yellow pigment diffuses into medium | pale mouse gray; edges light mouse gray; off-white edges | wax yellow center turning into dirty olive citrine close to the edges |
| 16 | good growth and sporulation | vegetative mycelium chamois; sporulation off-white with mouse gray patches; vegetative mycelium at edges of colonies becomes yellow ocher | mustard yellow center turning to antimony yellow toward the edges |
| 17 | abundant; poor sporulation; light yellow pigment diffusing into medium | vegetative mycelium honey yellow; sporulated areas light mouse gray with off-white edges | olive ocher center turning to honey yellow toward edges |
| 18 | abundant; wrinkled; with surface cracks; good sporulation; light yellow diffusible pigment | mouse gray with few pale gray patches | fuscous; paler indentations immersed into the agar |
| 19 | good, flat, with ruffled edges; thin sporulation | vegetative mycelium cream buff; sporulated areas pallid mouse gray | cream buff |
| 20 | abundant; smooth, with ruffled edges; good sporulation; lumps near the center of colonies; very little clearing around the colonies | mouse gray at center and pale mouse gray near edges; off-white edges | deep grayish olive center changing to chamois and cream buff toward edges |
| 21 | abundant; with good sporulation | mouse gray | mouse gray |
| 22 | fair; no sporulation; light yellow pigment diffuses into the medium | Naples yellow | mustard yellow |

Unless otherwise indicated, the observations reported have been performed after a period of incubation of 14 days at 28° C. The characteristics of growth in these solid media are summarized in the Table above. Colors of upper surface and reverse are named according to Ridgway's Color Standards and Color Nomenclature, Washington, D.C., 1912.

The species *Streptomyces* X-1092 described herein includes all strains of streptomyces which form a compound of the Formula I and which cannot be definitely differentiated from the strain NRRL 8047 and its subcultures including mutants and variants. The compound of the Formula I is identified herein and after this identification is known, it is easy to differentiate the strains producing a compound of the Formula I from others.

*Streptomyces* sp. X-1092, when grown under suitable conditions, produces a compound of the Formula I. A fermentation broth containing *Streptomyces* sp. X-1092 is prepared by inoculating spores or mycelia of the compound of the Formula I - producing organism into a suitable medium and then cultivating under aerobic conditions. For the production of a compound of the Formula I, cultivation on a solid medium is possible but for production in large quantities cultivation in a liquid medium is preferable. The temperature of the cultivation may be varied over a wide range, 20°–35° C, within which the organism may grow but a temperature of 26°–30° C and a substantially neutral pH is preferred. In the submerged aerobic fermentation of the organism for the production of a compound of the Formula I, the medium may contain as the source for carbon, a commercially available glyceride oil or a carbohydrate such as glycerol, glucose, maltose, lactose, dextrin, starch, etc. in pure or crude states and as the source of nitrogen, an organic material such as soybean meal, distillers solubles, peanut meal, cotton seed meal, meat extract, peptone, fish meal, yeast extract, corn steep liquor, etc. and when desired inorganic sources of nitrogen such as nitrates and ammonium salts and mineral salts such as ammonium sulfate, magnesium sulfate and the like. It also may contain sodium chloride, potassium chloride, potassium phosphate and the like and buffering agents such as sodium citrate, calcium carbonate or phosphates and trace amounts of heavy metal salts. In aerated submerged culturing procedures, an anti-foam agent such as liquid paraffin, fatty oils or silicone compounds is used. More than one kind of carbon source, nitrogen source or anti-foam source may be used for production of a compound of the Formula I. Generally the cultivation is continued until at least several hundred mcg/ml of a compound of the Formula I has accumulated in the medium.

The following Examples will serve to illustrate this invention without limiting it thereto.

EXAMPLE 1

Spores of *Streptomyces* sp. X-1092, were added to 6-liter Erlenmeyer flasks containing 2 liters of Trypticase soy broth (Baltimore Biological Laboratories). The flasks were incubated at 28° for 76 hours on a rotary shaker [240 rpm with a 2 inch stroke]. Four liters of inoculum was added to 200 liters of fermentation medium containing (in g/liter): $K_2HPO_4$, 7.0; $KH_2PO_4$, 3.0; $(NH_4)_2SO_4$, 1.0; sodium citrate, 0.5; $MgSO_4 \cdot 7H_2O$, 0.1; and D-glucose, 2.0 (autoclaved separately). The culture was incubated at 20° in a 380-liter fermentor, aerated at 113 liters per minute and agitated at 260 rpm. Silicone anti-form (Dow Corning AF) was added as needed to control frothing. After 66 hours of incubation, the fermentation broth was filtered through infusorial earth.

EXAMPLE 2

The clarified broth from two 200 liter fermentations was applied to 50 liters Dowex 50WX-4 resin, styrene-divinyl benzene-sulfonic acid ion exchange resin Ca 50–100 mesh, in the H+ form. After washing with 200 liters distilled water, the resin was eluted with 400 liters 5% aqueous pyridine solution. The eluate which contained 33 g solids was evaporated under reduced pressure to 2 liters, the pH adjusted to 2.5 by addition of 5N HCl and the solution applied to a column (70 cm ht) containing 2.5 liters Bio-Rad AG50WX-4 resin, styrene-divinyl benzene-sulfonic acid ion exchange resin, 100–200 mesh, in the Na+ form, which had been equilibrated with 0.2M sodium phosphate-citrate buffer, pH 4.2. The resin was then eluted with the same buffer and the activity was obtained at an elution volume of 11–13 liters. This fraction was desalted by readsorption of the antimetabolite onto 1.2 liters Bio-Rad AG50WX-4 resin, 50–100 mesh, in the H+ form followed by elution with 10% aqueous pyridine solution. The eluate was evaporated under reduced pressure to a small volume, the concentrate was treated with charcoal, the filtrate from the charcoal step was again evaporated and 1-(S)-hydroxy-2-(S,S)-valylamido-cyclobutane-1-acetic acid was crystallized from ethanol-water (9-1): m.p. 247°–250°; $[\rho]_D 25 + 8.4$ (c 1, $H_2O$), $-31.2$ (c 1, 5N HCl); $pK_1$ 3.8, $pK_2$ 7.5; ir (Kbr disk) 3365 and 3240 (OH and amide NH), 1660 and 1520 (sec amide), 1615 and 1390 cm$^{-1}$ (carboxylate); nmr ($D_2O$, 20 mg, ext TMS),

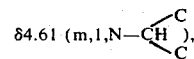

4.23 (d,1 J = 6Hz, 2.92 (3.18 with DCl)

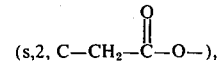

2.30–2.80 (m,5),

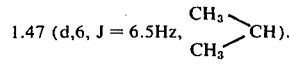

Anal. calcd for $C_{11}H_{20}N_2O_4$: C 54.03, H 8.25 N 11.47. Found: C 54.11, H 8.40, N 11.57.

EXAMPLE 3

As indicated above the compound of the Formula I and its salts are active against gram positive bacteria. Listed in Table 1 which follows are the inhibition zone diameters (mm) for several illustrative organisms as determined by agar-diffusion testing. As is apparent from the foregoing properties, the antibiotic of the Formula I is useful for suppressing the growth of gram positive organisms.

The antimicrobial spectrum of 1-(s)-hydroxy-2-(S,S)-valylamido-cyclobutane-1-acetic acid was measured in a chemically defined medium *a* by the paper disc agar-diffusion technique. The results are given in Table 1. The activity was limited to gram positive organism.

Table 1

| Antimicrobial Spectrum | |
|---|---|
| Test Organism | Inhibition zone diameter (mm) |
| Bacillus cereus ATCC-6464 | 60 |
| Bacillus sp. ATCC-27860 | 25 |
| Bacillus subtilis NRRL-558 | 34 |
| Streptomyces cellulosae ATCC-3313 | 34 |
| Micrococcus glutamicus ATCC-13761[b] | 20 |
| Escherichia coli B | 0 |
| Pseudomonas ovalis NRRL-22 | 0 |
| Candida albicans NRRL-477[b] | 0 |
| Pullularia pullulans QM-279c | 0 | a. Paper-disc agar-diffusion assays were performed with 12.7 mm discs each containing 12 m$\mu$ of a compound of the Formula I in Davis Minimal Agar.

b. Biotin was added to the medium at 100 g liter to insure ample growth of these test organisms.

The compound of the Formula I also evidenced antimetabolite activity. This activity was determined by counter diffusion methods which have been described in the literature in Journal of Antibiotics, Volume 27, pp. 229–233, 1974. against *Streptomyces cellulosae*. The activity of the compound of the Formula I was non-competitively reversed by the addition of either L-cysteine or L-cystine to the medium. Partial reversals were observed with either L-methionine or D,L-homocysteine. Other common amino acids, nucleosides and water soluble vitamins did not reverse the activity of a compound of the Formula I. In addition glutathione and dithiothreitol did not reverse the inhibition, so it can be concluded that the reversal by cysteine is not due to chemical inactivation by thiols.

Only slight reversal of inhibition against the three species of Bacilli and *Micrococcus glutamicus* was observed with L-methionine, L-cystine and L-cysteine; no reversal was observed with other common amino acids mucleosides and/or water soluble vitamins.

As is indicated above, the compound of the Formula I is prepared under submerged aerobic conditions. Preferably submerged fermentation in tanks is used for production of substantial quantities of the X-1092 antibiotic in accordance with conventional procedures. Small quantities of antibiotic are obtained by shake-flask culture. As is customary in aerobic submerged culture processes, sterile air is blown through the culture medium. For efficient growth of the organism and production of the antibiotic of the Formula I, the volume of air employed in the production is above 0.1 volume of air per minute per volume of culture medium. Optimum growth occurs when the volume of air employed is between 0.6 and one volume of air per minute per volume of culture production medium. The production of antibiotics can be followed during the fermentation by testing samples of the broth for antibiotic activity against organisms known to be sensitive to the antibiotic. The bioassay is conveniently effected by paper disc assay on agar plates.

As is the custom, maximum antibiotic production occurs within 2–6 days in either large tank or shake-flask fermentation. Commonly maximum production of antibiotic activity is realized within 5–6 days.

Following its production under submerged aerobic conditions the compound of the Formula I can be recovered from the fermentation broth by methods commonly employed in the fermentation art. The anitbiotic activity produced during fermentation of a compound of the Formula I-producing organism occurs in the antibiotic broth. Accordingly, isolation techniques employed in the production of such antibiotics are designed to permit maximum recovery of the antibiotic from the broth. Thus, for example, mycelia and undissolved solids are removed from the fermentation broth by conventional means such as filtration and the antibiotic of the Formula I is recovered from the filtered broth by techniques such as ion exchange or adsorption.

The compound of the Formula I having the basic amino group and the acid COOH group can form salts with both acids and bases. It is easily soluble in alcaline solutions such as aqueous solutions of alkaline metal and alkaline earth metal hydroxides. Thus, solutions of a compound of the Formula I in aqueous sodium hydroxide or calcium hydroxide forms the sodium or calcium salt respectively which can be isolated by conventional procedures. In like manner are formed salts of organic bases such as amine salts and the like. Similarly, the compound of the Formula I can form salts with acidic substances and such substances can be prepared by conventional techniques with such pharmaceutically acceptable acids as hydrochloric acid, hydrobromic acid, sulfuric acid and the like. All that is required of the salt is that it provide a pharmaceutically acceptable salt of a compound of the Formula I.

As is indicated above, compounds of the Formula I and its salts possess the property of adversely affecting the growth of certain Gram-positive bacteria. It is useful in wash solutions for sanitary purposes as in the washing of hands and the cleaning of equipment, floors or furnishings of contaminated rooms or laboratories; It is useful also for suppressing the growth of sensitive organisms in plate assays and other microbiological media.

We claim:

1. A compound of the formula:
1-(s)-hydroxy-2-(S,S)-valylamido-cyclobutane-1-acetic acid and its pharmaceutically acceptable salts.

* * * * *